United States Patent
Stierstorfer (10) Patent No.: US 10,504,634 B2
(45) Date of Patent: Dec. 10, 2019

(54) METHOD AND DEVICE FOR SETTING A SPATIAL INTENSITY DISTRIBUTION OF AN X-RAY BEAM

(71) Applicant: Siemens Healthcare GmbH, Erlangen (DE)

(72) Inventor: Karl Stierstorfer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 237 days.

(21) Appl. No.: 15/652,406

(22) Filed: Jul. 18, 2017

(65) Prior Publication Data
US 2018/0033514 A1    Feb. 1, 2018

(30) Foreign Application Priority Data

Jul. 29, 2016 (DE) .......... 10 2016 213 990

(51) Int. Cl.
| | | |
|---|---|---|
| G21K 1/10 | (2006.01) | |
| A61B 6/06 | (2006.01) | |
| A61B 6/03 | (2006.01) | |
| G21K 1/02 | (2006.01) | |
| A61B 6/00 | (2006.01) | |

(52) U.S. Cl.
CPC ............... *G21K 1/10* (2013.01); *A61B 6/032* (2013.01); *A61B 6/06* (2013.01); *A61B 6/4035* (2013.01); *G21K 1/025* (2013.01)

(58) Field of Classification Search
CPC ........ G21K 1/025; G21K 1/10; A61B 6/4035; A61B 6/032; A61B 6/06
See application file for complete search history.

(56) References Cited

U.S. PATENT DOCUMENTS

| 5,949,850 A | 9/1999 | Cha-Mei |
|---|---|---|
| 2008/0080674 A1 | 4/2008 | Kashiwagi |

(Continued)

FOREIGN PATENT DOCUMENTS

| DE | 102010019991 A1 | 11/2011 |
|---|---|---|
| WO | WO 2014180901 A1 | 11/2014 |

OTHER PUBLICATIONS

German Office Action dated Oct. 10, 2018.
(Continued)

*Primary Examiner* — David P Porta
*Assistant Examiner* — Fani Boosalis
(74) *Attorney, Agent, or Firm* — Harness, Dickey & Pierce, P.L.C.

(57) ABSTRACT

In a method and device for setting a spatial intensity distribution of an X-ray beam, an X-ray beam is generated by an X-ray tube. A beam path of the X-ray beam is guided in a direction of propagation by a form filter including a plurality of lamella plates which taper to a focal point such that, for each of the lamella plates, at least one straight line running through the respective lamella plate and forming a first direction of the lamella plate is aligned with the focal point. The first directions of the lamella plates of the form filter are aligned relative to the beam path. As a result of the alignment, parts of the X-ray beam are absorbed. Finally, the spatial intensity distribution of the X-ray beam is set in the direction of propagation by the absorption due to the lamella plates.

19 Claims, 6 Drawing Sheets

(56) References Cited

U.S. PATENT DOCUMENTS

| | | | |
|---|---|---|---|
| 2010/0008472 A1* | 1/2010 | Bohn | A61N 5/1042 |
| | | | 378/150 |
| 2010/0254516 A1* | 10/2010 | Harding | G21K 1/025 |
| | | | 378/147 |
| 2011/0274238 A1 | 11/2011 | Maschke | |
| 2013/0272501 A1 | 10/2013 | Den | |
| 2015/0182179 A1 | 7/2015 | Edic | |
| 2016/0081636 A1 | 3/2016 | Kremer | |

OTHER PUBLICATIONS

Stayman et al.,Fluence-field modulated x-ray CT using multiple aperture devices, SPIE 9783-32, 2016; 2016.
German Office Action 10 2016 213 990.8 dated Apr. 5, 2017.

* cited by examiner

METHOD AND DEVICE FOR SETTING A SPATIAL INTENSITY DISTRIBUTION OF AN X-RAY BEAM

PRIORITY STATEMENT

The present application hereby claims priority under 35 U.S.C. § 119 to German patent application number DE 102016213990.8 filed Jul. 29, 2016, the entire contents of which are hereby incorporated herein by reference.

FIELD

At least one embodiment of the invention generally relates to a method for setting a spatial intensity distribution of an X-ray beam, wherein an X-ray beam is generated by an X-ray tube, wherein a beam path of the X-ray beam is guided in a direction of propagation by a form filter, and wherein a spatial intensity distribution of the X-ray beam is set in the direction of propagation. At least one embodiment of the invention also generally relates to a device for setting a spatial intensity distribution of an X-ray beam, comprising a form filter and a control unit.

BACKGROUND

In a computer tomograph (CT) the radiation used for medical imaging is generated by an X-ray tube. The spatial area of the anode of the X-ray tube, in which the X-ray radiation used for imaging is physically generated, can be assumed as being almost point-shaped in relation to the dimensions of the CT and the dimensions of a region of the body to be examined of a patient. The beam path of the X-ray radiation essentially fans radially from the generation point defined in this way, wherein the solid angle range, in which irradiation of the X-ray radiation occurs in the first place, can be influenced or restricted by the geometry of the anode and optionally a subsequent diaphragm arrangement.

The X-ray tube is arranged in the CT on a slewing ring which performs a rotational movement about an axis during operation of the CT. The region of the body of a patient to be imaged by the CT is positioned along this axis. The beam path of the X-ray tube is then guided in a fan shape, optionally with the aid of appropriate diaphragms, from the generation point into the interior space surrounded by the slewing ring.

For optimally high image resolution by the CT, an optimally sharp contrast is desirable in each case in every single image recording, which is produced by an X-ray beam generated in a particular angular position or in a narrow angular range of the generation point. Since the contrast in an individual scan is produced by the different absorption level for X-ray radiation, which the individual tissue layers that are to be imaged have, and since, further, the tissue to be imaged in each case during a scan is precisely defined, firstly an optimally high intensity of the incident X-ray radiation is desirable for an increase in the contrast and therewith an improvement in the noise. Secondly, for medical reasons this radiation intensity should be limited, however, at least averaged over time, for a specified region of the body.

In order to limit the intensity of the X-ray radiation a CT often has a number of absorption filters which are arranged in the vicinity of the generation point, and therefore limit the intensity striking the patient from the start. A constant absorption profile achieved hereby and the accompanying predefined limitation of the radiation intensity is not usually capable of adequately taking into account anatomical peculiarities of the region of the body to be examined, however. This should be considered, in particular, against the background that the X-ray tube rotates around the region of the body of the patient to be imaged during operation of the CT.

An anatomical peculiarity can therefore result, for example, from an eccentric position of the region of the body in respect of the axis of rotation, but also from the fact that radiation striking the front of the patient covers an essentially shorter distance through the patient, and consequently undergoes significantly less absorption, than radiation that strikes the side of the patient, which propagates, for example, from one shoulder to the opposite shoulder. The difference in the level of absorption solely due to the different distances covered in the body of the patient can amount to more than a factor of 100. Previous absorption filters do not provide a satisfactory solution to this. Furthermore, a variation in the spatial absorption profile, in particular during a CT scan, desired for the reasons above is currently neither provided nor feasible.

SUMMARY

At least one embodiment of the invention discloses a method by which a spatial intensity distribution of an X-ray beam can be variably set. Furthermore, in at least one embodiment of the invention, a spatial intensity distribution can be set for an X-ray beam via a device.

At least one embodiment of the invention is directed to a method for setting a spatial intensity distribution of an X-ray beam, wherein an X-ray beam is generated by an X-ray tube, wherein a beam path of the X-ray beam is guided in a direction of propagation by a form filter having a plurality of lamella plates which taper to a focal point in such a way that for each of the lamella plates at least one straight line running through the respective lamella plate and forming a first preferred direction of the lamella plate is aligned with the local point, wherein the first preferred directions of the lamella plates of the form filter are aligned relative to the beam path, wherein as a result of the alignment of their first preferred directions by the lamella plates parts of the X-ray beam are absorbed, and wherein a spatial intensity distribution of the X-ray beam is set in the direction of propagation by the absorption due to the lamella plates.

At least one embodiment of the invention is directed to a device for setting a spatial intensity distribution of an X-ray beam, comprising a form filter having a first plurality of lamella plates, which taper to a focal point in such a way that for each of the lamella plates at least one straight line running through the respective lamella plate and forming a first preferred direction of the lamella plate is aligned with the focal point, and a control unit, which is adapted to set by way of an alignment of the first preferred directions of the lamella plates of the form filter relative to the beam path an absorption of parts of the X-ray beam by the lamella plates a spatial absorption profile of the X-ray beam can be set.

Advantageous and in part separately inventive embodiments are the subject matter of the claims and the following description.

BRIEF DESCRIPTION OF THE DRAWINGS

An example embodiment of the invention will be illustrated in more detail below with reference to the drawings, in which in each case schematically.

Mutually corresponding parts and variables are provided with identical reference numerals in all figures respectively.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a method for setting a spatial intensity distribution of an X-ray beam, wherein an X-ray beam is generated by an X-ray tube, wherein a beam path of the X-ray beam is guided in a direction of propagation by a form filter having a plurality of lamella plates which taper to a focal point in such a way that for each of the lamella plates at least one straight line running through the respective lamella plate and forming a first preferred direction of the lamella plate is aligned with the local point, wherein the first preferred directions of the lamella plates of the form filter are aligned relative to the beam path, wherein as a result of the alignment of their first preferred directions by the lamella plates parts of the X-ray beam are absorbed, and wherein a spatial intensity distribution of the X-ray beam is set in the direction of propagation by the absorption due to the lamella plates.

At least one embodiment of the invention is directed to a device for setting a spatial intensity distribution of an X-ray beam, comprising a form filter having a first plurality of lamella plates, which taper to a focal point in such a way that for each of the lamella plates at least one straight line running through the respective lamella plate and forming a first preferred direction of the lamella plate is aligned with the focal point, and a control unit, which is adapted to set by way of an alignment of the first preferred directions of the lamella plates of the form filter relative to the beam path an absorption of parts of the X-ray beam by the lamella plates a spatial absorption profile of the X-ray beam can be set.

A spatial intensity distribution of the X-ray beam should here, in particular, be taken to mean the distribution of the intensity of the X-ray beam at a given distance from the site of generation of the X-ray beam in the direction of propagation. A lamella plate should, in particular, be taken to mean a planar workpiece whose local thickness is negligible at least when compared to a further dimension. The local thickness of a lamella plate is preferably less than half the distance from an adjacent lamella plate. The direction of propagation of the X-ray beam can also be restricted by a number of diaphragms before reaching the form filter in the direction of propagation.

The lamella plates can basically be designed to be flat or have a curve along at least one of the two local surface directions. A first preferred direction of a lamella plate should then be taken to mean a straight line which runs through the lamella plate over a relatively long section in at least one of the local surface directions (in other words, does not just touch the relevant lamella plate tangentially in a curve), wherein the straight line tapers toward the focal point. A large number, particularly preferably a continuous set, of straight lines running through the lamella plate, is preferably aligned with the preferred point for each of the lamella plates respectively. The alignment of the lamella plates in respect of the focal point means that an X-ray beam, which propagates radially or in a cone shape from the focal point, strikes the lamella plates aligned with the focal point at most in a negligibly small front edge.

If the beam path of an X-ray beam, which is to be filtered via the form filter, is now guided such that the X-ray beam propagates largely radially from the focal point of the form filter, the form filter does not achieve an appreciable attenuation of the intensity of the X-ray beam. A relative movement of the form filter in respect of the site of generation of the X-ray beam, however, means that the focal point, with which the lamella plates are aligned, no longer coincides with the region from which the X-ray beam radially propagates. As a consequence of their alignment with the focal point the lamella plates hereby absorb some of the X-ray radiation since now at least some of the lamella plates no longer run locally parallel to the beam path, but have a non-diminishing normal component in respect thereof.

Depending on the type of relative movement, a largely uniform absorption over the entire form filter can be set, or particular central regions of the beam path can be chosen in which the absorption of the radiation intensity of the X-ray radiation turns out lower, whereas the attenuation of the intensity turns out to be greater with increasing distance from the central region. A spatial intensity distribution of the X-ray radiation downstream of the form filter can now be adjusted hereby as well as by individual variations in the construction of the lamella plates.

The form filter is preferably made from a material that is as uniformly absorbent as possible for the X-ray beams in the anticipated spectrum, preferably an element having a high atomic number, such as, for example, lead, tantalum, tungsten or a material having comparable absorption properties in order, firstly, to be able to set the intensity distribution via the absorption directly by the geometry of the lamella plates in the form filter and to minimize the beam hardening in the process, and in order, secondly, to prevent the lamella plates from acting transparently for particularly high-energy X-ray radiation, and therefore the absorption can no longer be effectively controlled.

Preferably at least some of the X-ray radiation is generated at a generation point in the X-ray tube, wherein a spatial intensity distribution is set in that the first preferred directions of the lamella plates are each aligned in respect of the generation point, and wherein an initial position of the form filter is defined by the alignment of the first preferred directions of the lamella plates with the generation point. In particular, a large number of straight lines each forming a first preferred direction is aligned with the focal point and therefore with the generation point for each of the lamella plates in the initial position. The alignment of the first preferred directions in respect of the generation point can then be achieved particularly easily by way of corresponding positioning of the focal point, and this is particularly easy to control.

A spatial intensity distribution having maximum intensity is advantageously set hereby by the form filter in the initial position. In the initial position, the X-ray radiation strikes the lamella plates in each case at most in a negligible narrow front edge, so the attenuation of the intensity by the form filter is minimal, and a maximum intensity is set hereby.

The intensity is expediently reduced by the outer border regions of the form filter due to an axial displacement of the form filter from the initial position in respect of the generation point and/or due to a rotation of the form filter while maintaining the alignment of at least one of the first preferred directions of a lamella plate with the generation point. In particular, the intensity is reduced to a lesser extent by the central regions of the form filter than by the outer border regions.

With an axial displacement along one of the first preferred directions of a lamella plate of the form filter, the focal point of the form filter and the generation point of the X-ray radiation diverge to the extent that for lamella plates, which are aligned almost parallel with the direction of displacement, the displacement is of no or scant consequence, for which reason the attenuation of the intensity remains very low here. As a consequence of the alignment with the focal point, more remote lamella plates are no longer parallel with the direction of displacement, however, for which reason they have a non-diminishing normal component in respect of the generation point. This means that an absorption occurs for X-rays, which issue from the generation point, in these regions. A comparable effect can be achieved in that the form filter is rotated about an axis in such a way that in the central region the lamella plates remain aligned largely parallel with the beam path.

It has also proven to be advantageous if the intensity over the entire region of the form filter is reduced by a rotation of the form filter without maintaining the alignment of a first preferred direction of a lamella plate with the generation point. In the case of planar lamella plates, a rotation of this kind can be achieved, for example, by a rotation about an axis which is parallel to a plurality of lamella plates. With a rotation of this kind none of the lamella plates remains even only approximately parallel to the beam path, whereby an attenuation of the intensity of the X-ray radiation is achieved by each of the lamella plates, and a spatial intensity distribution of lower intensity is set hereby.

For the device it has also proven to be advantageous if the first plurality of lamella plates is constructed and aligned in the form filter in such a way that a second preferred direction can be defined perpendicular to the preferred direction in each lamella plate using a straight line that runs through the respective lamella plate, wherein for each two lamella plates their second preferred directions are parallel to each other. Specifically, this means: a particular first preferred direction runs to the focal point in one lamella plate, and a second preferred direction can be found which is formed by a straight line that again runs through the lamella plate and is perpendicular to the first preferred direction. The second preferred directions can therefore be given, for example, by straight lines in the front edges of the lamella plates. If the second preferred directions of the individual lamella plates are accordingly each parallel to each other for the first plurality of lamella plates, the form filter then has a type of fan-like structure.

It has also proven advantageous for the device if the form filter comprises a second plurality of lamella plates which taper to the focal point in such a way that for each of the lamella plates of the second plurality, at least one straight line running through the respective lamella plate and forming a first preferred direction of the lamella plate is aligned with the focal point, wherein the lamella plates of the first plurality intersect the lamella plates of the second plurality. The intersection lines, which are formed by an intersection of a lamella plate of the first plurality with a lamella plate of the second plurality, preferably run in the direction of the focal point. The lamella plates of the first plurality and the lamella plates of the second plurality hereby form a grid-like structure in the form filter, and this improves setting of a spatial intensity distribution owing to the more complex geometry of the form filter.

In a further advantageous embodiment of the device the lamella plates of the form filter describe the circumferential surfaces of a set of concentric truncated cones. In particular, truncated cones with an elliptical base area are also incorporated here. The truncated cones preferably each correspond to cones whose apex is located in the focal point. The individual preferred directions of a lamella plate run along the surface line of the truncated cone in the direction of the focal point. This kind of alternative geometry of the form filter is advantageous in particular if the beam path of the X-ray radiation was not restricted as early as before the pre-filter in a very flattened solid angular range.

Figure 1:
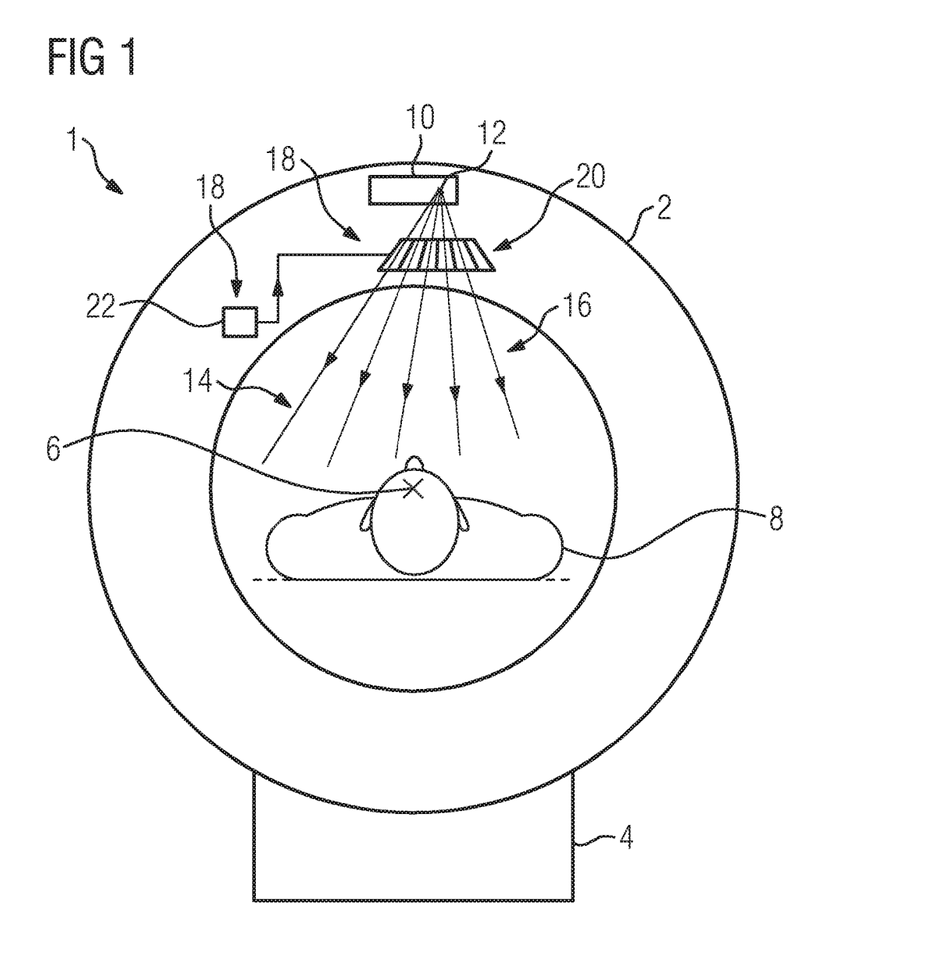
FIG. 1 shows in a cross-section a CT having a device for setting a spatial intensity distribution of the X-ray radiation.

FIG. 1 schematically shows in a cross-section a CT 1 which has a slewing ring 2 and a mounting frame 4. The slewing ring 2 is rotatably mounted in respect of the axis 6. During operation of the CT 1 a patient body 8 is positioned in the space surrounded by the slewing ring 2 in such a way that the axis 6 runs through the patient body 8. An X-ray tube 10 inter alia is arranged on the slewing ring 2 and this generates X-rays 14 in a generation point 12. The beam path 16 of the X-rays 14 runs from the generation point 12 in a fan shape in the direction of the patient body 8. The CT 1 accordingly has a device 18 for setting a spatial intensity distribution of the X-rays 14. The device 18 comprises a form filter 20 which is positioned in the immediate vicinity of the generation point 12 in the beam path 16, and a control unit 22. The control unit 22 sets the desired spatial intensity distribution of the X-rays 14 in a manner still to be described by way of appropriate positioning of the form filter 20 in respect of the beam path 16 in such a way that the radiation intensity striking the patient body 8 is optimum in respect of the image resolution as well as in respect of medical criteria at any time during operation of the CT 1.

Figure 2:
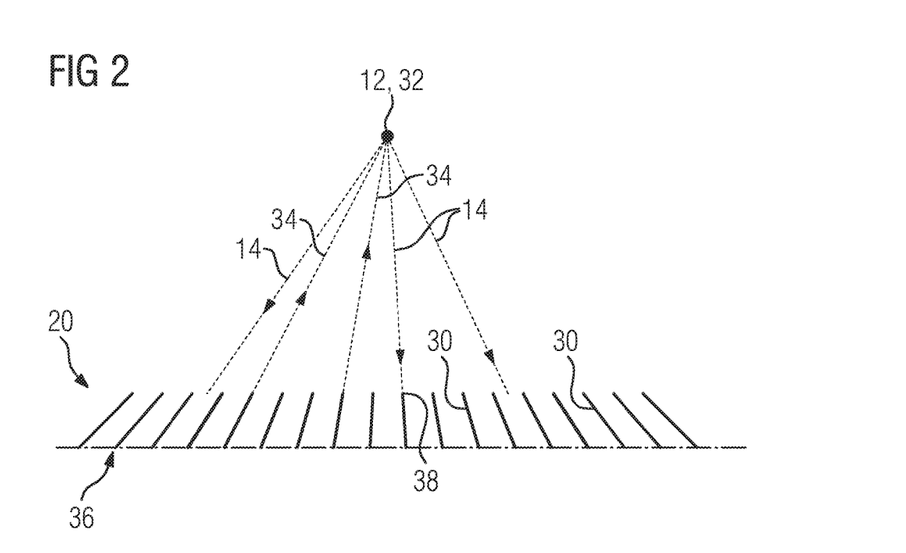
FIG. 2 shows in a cross-section the embodiment of a form filter of the device in FIG. 1.

FIG. 2 schematically shows in a cross-section an embodiment of a form filter 20. The form filter 20 should be positioned in the CT 1 in FIG. 1 such that the axis 6 is perpendicular to image plane. The form filter 20 comprises a first plurality of lamella plates 30. Each of the lamella plates 30 is formed flat and aligned with a focal point 32. Each of the lamella plates 30 has a first preferred direction 34 which is formed by a straight line running through the respective lamella plate 30 to the focal point 32. In an initial position 36 the form filter 20 is positioned in the beam path 16 in such a way that the generation point 12 of the X-ray tube 10 coincides with the focal point 32 with which the lamella plates 20 of the form filter 20 are aligned. When the form filter 20 is brought into the initial position 36, the intensity of the X-rays 14 is the maximum possible everywhere downstream of the form filter 20 since the lamella plates 30 are aligned directly with the generation point 12, and therefore do not affect the propagation of the X-rays 14 as a consequence of their flat form. Effects when X-rays 14 strike a front edge 38 of a lamella plate 30 can likewise be ignored here, such as a lack of a curve in the lamella plates 30 in a direction transverse to the image plane, since in many CT applications the X-rays 14 are guided with the aid of diaphragms into a solid angle range whose expansion in the direction of the axis 6 of the CT 1 is almost negligible compared to the expansion in the plane of rotation of the slewing ring 2.

Figure 3:
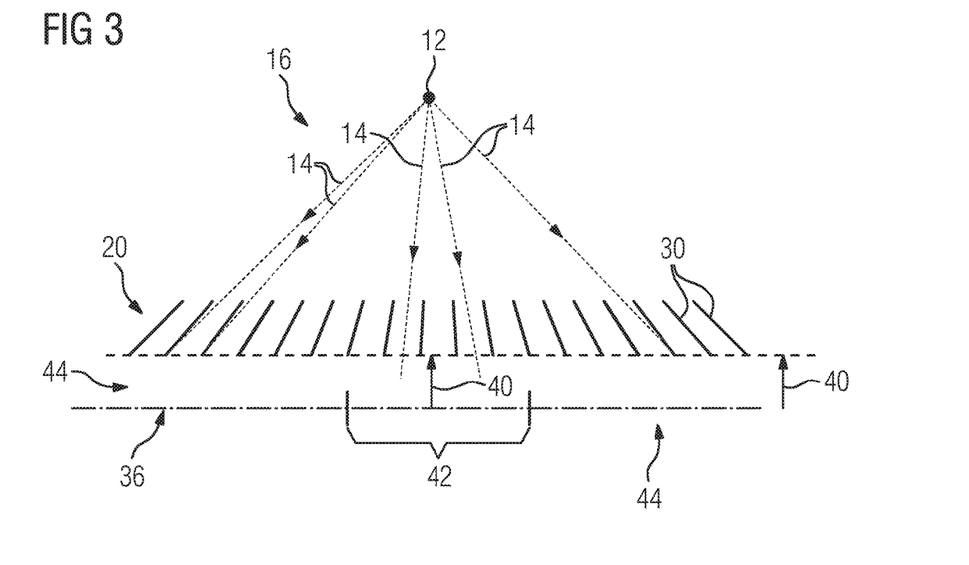
FIG. 3 shows in a cross-section an axial displacement of the form filter in FIG. 2 from an initial position in order to set a spatial intensity distribution.
Figure 4:
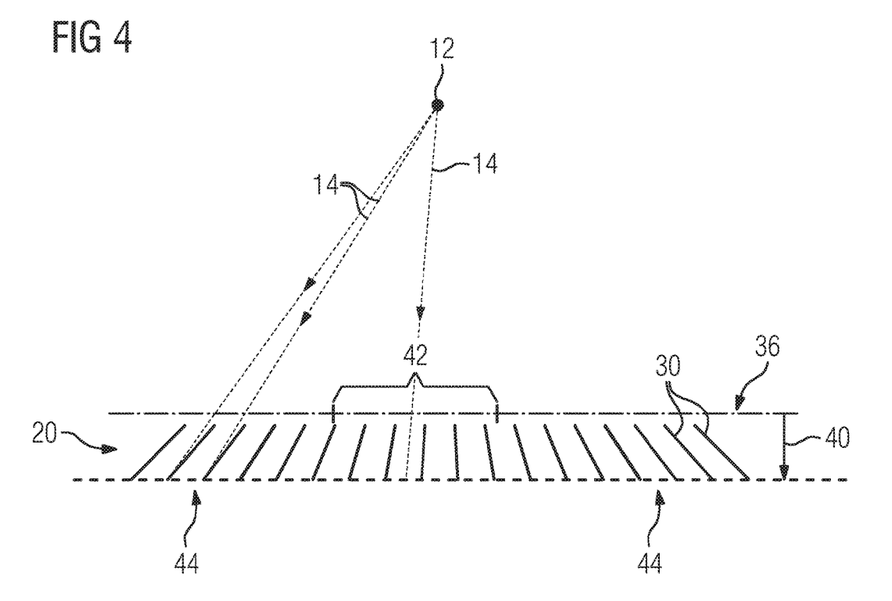
FIG. 4 shows in a cross-section a further axial displacement of the form filter in FIG. 2 from an initial position in order to set a spatial intensity distribution.

FIG. 3 and FIG. 4 each schematically show in a cross-section how regions of attenuated intensity can be set in the beam path 16 by a displacement of the form filter 20 from the initial position 36. In FIG. 3 the form filter 20 is pushed in respect of the initial position 36 in a normal direction 40 toward the generation point 12 of the X-ray tube 10. This displacement along the normal direction 40 does not have any appreciable effects in the central region 42 of the beam path 16 since there the alignment of the lamella plates still generates approximately in the direction of the generation point 12. In the border regions 44 of the beam path 16, however, the altered alignment of the lamella plates 30 is more noticeable, X-rays 14 are absorbed in the border regions 44 more frequently by a lamella plate 30 during propagation, so the intensity in the border regions 44 is attenuated with increasing distance from the central region 42. FIG. 4 shows how a similar effect is achieved by a displacement in the opposite direction to the normal direction 40.

Figure 5:
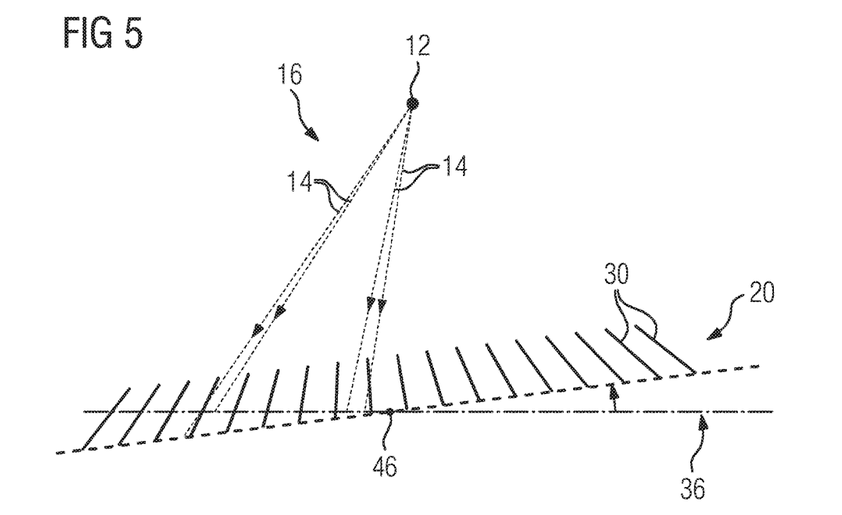
FIG. 5 shows in a cross-section a rotation of the form filter in FIG. 2 in the image plane in order to set a spatial intensity distribution.
Figure 6:
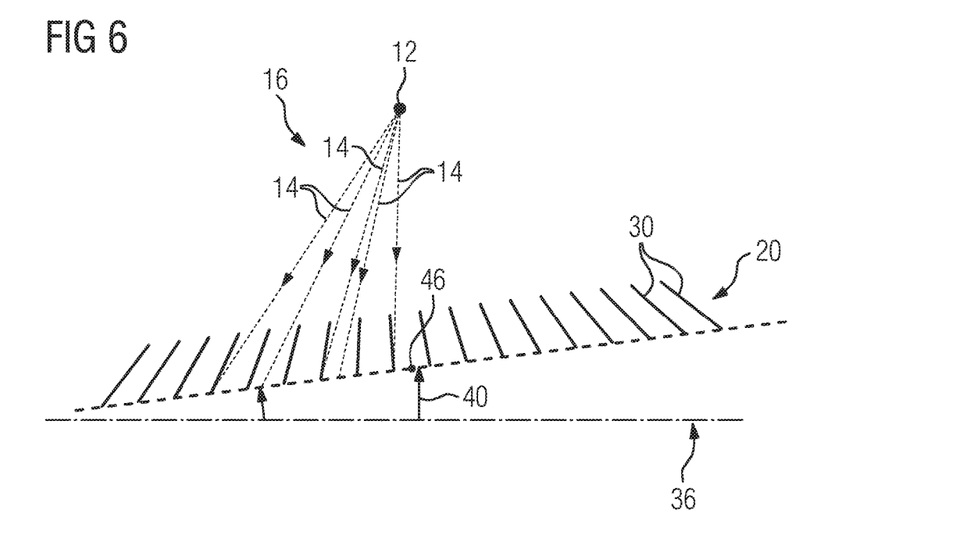
FIG. 6 shows in a cross-section a combination of the displacement of the form filter in FIG. 3 with the rotation of the form filter in FIG. 5 in order to set a spatial intensity distribution.

FIG. 5 shows schematically in a cross-section how by way of a rotation of the form filter 20, an attenuation of the intensity of the X-rays can be achieved throughout the beam path 16. The form filter 20 is rotated in respect of an axis of rotation 46. The axis of rotation 46 runs parallel to each single one of the lamella plates 30, and should be chosen as centrally as possible in the form filter 20 in respect of the generation point 12. FIG. 6 schematically shows in a cross-section how the intensity of the X-rays 14 can be attenuated in the region of the entire beam path 16 by a combination of the displacement illustrated by FIG. 3 and the rotation illustrated by FIG. 5.

Figure 7:
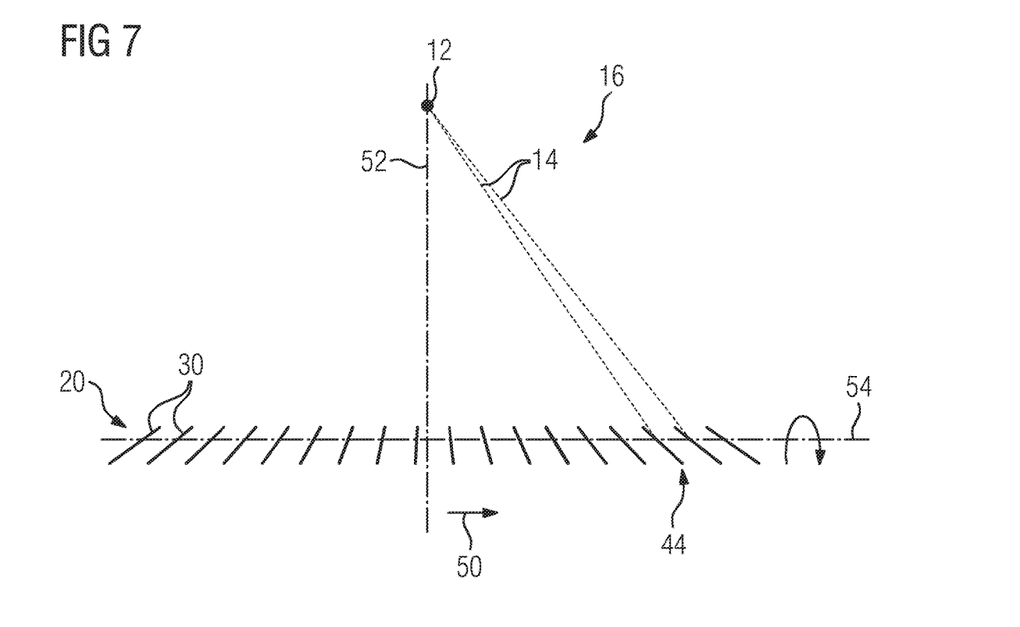
FIG. 7 shows in a cross-section a rotation of the form filter in FIG. 2 about an axis in the image plane in order to set a spatial intensity distribution.

Furthermore, an attenuation of the intensity in the region of the entire beam path 16 can also be set by a rotation about an axis that does not run parallel to the lamella plates 30. A longitudinal direction 50 can be defined in the form filter 20 by the lamella plates 30, for example as a consequence of the symmetry, and this direction is perpendicular to a mirror plane 52 in respect of which the lamella plates 20 are symmetrically arranged. A rotation in respect of a longitudinal axis 54, which runs in the longitudinal direction 50, enables a spatial intensity profile with an attenuated intensity for the border regions 44 of the beam path 16. This is shown schematically in FIG. 7 in a cross-section.

Figure 8:
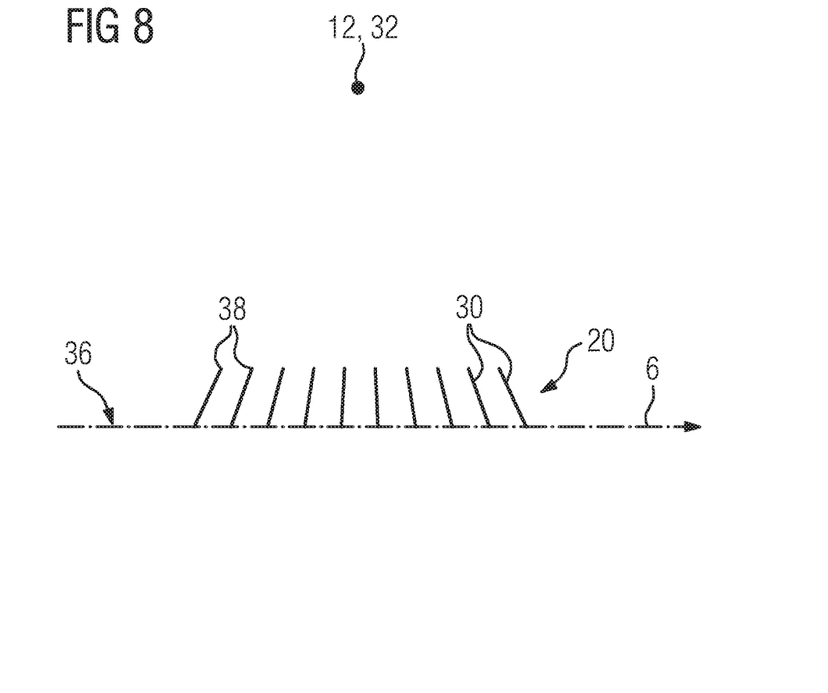
FIG. 8 shows in a longitudinal section one possible embodiment of the form filter in FIG. 1.

FIG. 8 schematically shows in a longitudinal section a form filter 20 which has a plurality of lamella plates 30 whose front edges 38 are each perpendicular to the axis 6 about which the slewing ring 2 rotates during operation of the CT 1. The flat lamella plates 30 are aligned with the focal point 32 which in an initial position 36 of the form filter 20 coincides with the generation point 12 of the X-ray tube 10 in which the X-rays 14 are generated. An alignment of this kind of the lamella plates 30 means the maximal possible intensity of the X-rays 14 can be set by the form filter 20 in the initial position 36. Local attenuations of the intensity in the beam path 16 can be achieved by displacements of the form filter along or counter to a normal direction 40, as well as by rotations in respect of an axis of rotation which has at least one subcomponent perpendicular to the image plane.

A form filter 20 having two sets of lamella plates 30 is also conceivable for setting a spatial intensity distribution of the X-rays 14 here. A first plurality of lamella plates 30 is aligned in such a way that their front edges 38 are parallel to the axis 6 about which the slewing ring 2 rotates during rotation of the CT 1, a second plurality of lamella plates 30 is aligned in such a way that their front edges 38 are perpendicular to axis 6.

Figure 9:
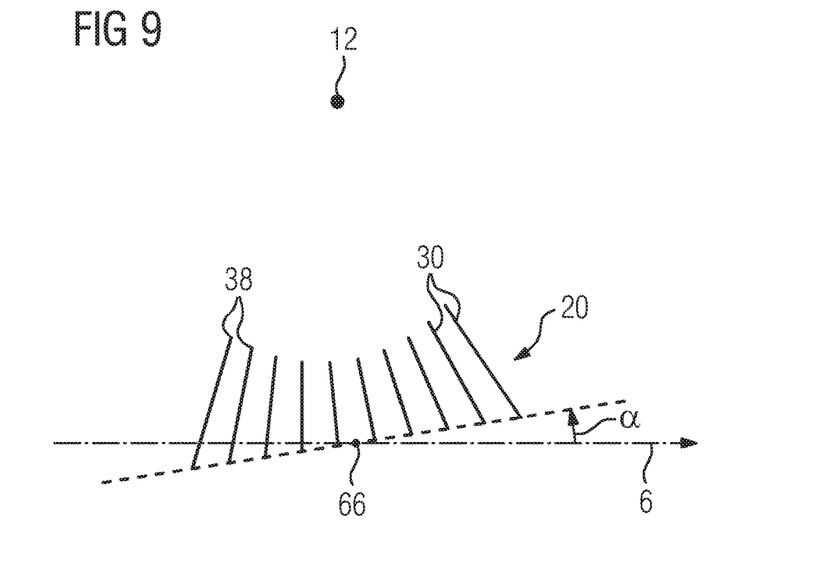
FIG. 9 shows in a longitudinal section a further embodiment of the form filter in FIG. 1.

FIG. 9 schematically shows in a longitudinal section a form filter 20 which has lamella plates 30 which each have a different height in respect of the alignment. The attenuation of the intensity can be set as a function of an angle of rotation α in respect of an axis of rotation 66 by the variation in the height of the lamella plates over the form filter 20. A variation of this kind in the height of the lamella plates 30 in the direction of the alignment is also conceivable for lamella plates whose front edges 38 are parallel to axis 6.

Figure 10:
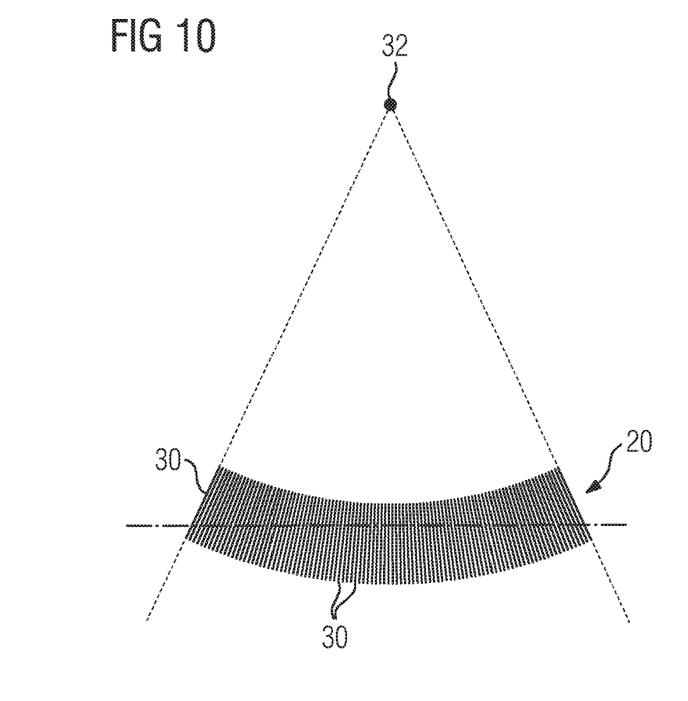
FIG. 10 shows in a cross-section an embodiment of the form filter in FIG. 1 with lamella plates spaced radially from the focal point.

FIG. 10 schematically shows in a cross-section a further possible embodiment of a form filter 20. Here the lamella plates 30 are each arranged radially at the same distance from the focal point 32, and each have the same height in the direction of the alignment. The lamella plates 30 can be planar here, or also be formed by the circumferential surfaces of concentric truncated cones.

Figure 11:
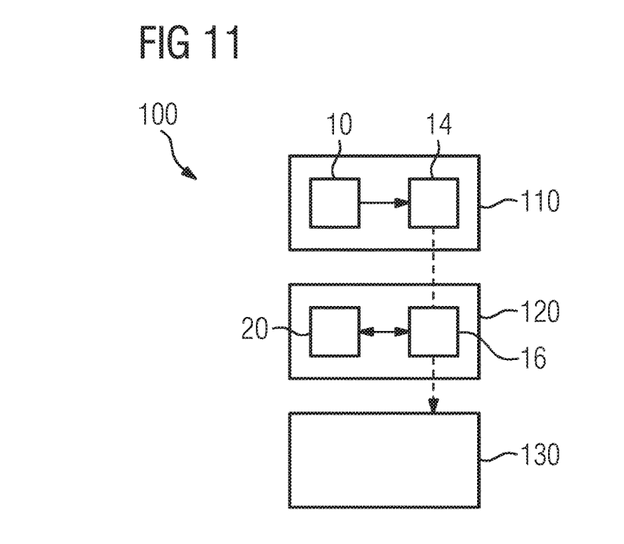
FIG. 11 shows in a block diagram a method for setting a spatial intensity distribution of an X-ray beam.

FIG. 11 schematically shows in a block diagram a method 100 for setting a spatial intensity distribution of an X-ray beam 14. In a first step 110 an X-ray beam 14 is generated by an X-ray tube 10. In a second step 120 a form filter 20, which comprises a plurality of lamella plates 30, is aligned relative to the beam path 16 of the X-ray beam 14. In the next step 130 parts of the X-ray beam 14 are absorbed owing to the alignment by the lamella plates 30, so a spatial intensity distribution of the X-ray beam 14 is set in the direction of propagation of the X-ray beam 14 hereby.

Although the invention has been illustrated and described in more detail by the preferred example embodiment, it is not limited by this example embodiment. A person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for setting a spatial intensity distribution of an X-ray beam, comprising:
   generating an X-ray beam via an X-ray tube;
   guiding a beam path of the X-ray beam in a direction of propagation by a form filter including a plurality of lamella plates which taper to a focal point such that, for each respective lamella plate of the plurality of lamella plates, at least one straight line running through each respective lamella plate and forming a first direction of the lamella plate is aligned with the focal point;
   aligning the first directions of the plurality of lamella plates of the form filter relative to the beam path, parts of the X-ray beam being absorbed as a result of the aligning of the first directions by the lamella plates; and
   setting the spatial intensity distribution of the X-ray beam in a direction of propagation established by the absorption of the parts of the X-ray beam due to the aligning of the first directions by the lamella plates.

2. The method of claim 1, further comprising:
   generating at least some of X-ray radiation of the X-ray beam at a generation point in the X-ray tube, wherein the spatial intensity distribution is set with the first directions of the plurality of lamella plates being each respectively aligned in respect of the generation point.

3. The method of claim 2, further comprising:
   defining an initial position of the form filter by the alignment of the first directions of the plurality of lamella plates with the generation point, wherein the spatial intensity distribution, including a maximum intensity, is set by the form filter in the initial position.

4. The method of claim 3, wherein due to an axial displacement of the form filter from at least one of the initial position in respect of the generation point and due to a rotation of the form filter while maintaining alignment of at least one of the first directions of a lamella plate with the generation point, the intensity is reduced by outer border regions of the form filter.

5. The method of claim 4, wherein the intensity over an entire region of the form filter is reduced by a rotation of the form filter without maintaining the alignment of a first direction of one of the plurality of lamella plates with the generation point.

6. The method of claim 3, wherein the intensity over an entire region of the form filter is reduced by a rotation of the form filter without maintaining alignment of a first direction of one of the plurality of lamella plates with the generation point.

7. The method of claim 2, wherein due to an axial displacement of the form filter due to a rotation of the form filter while maintaining alignment of at least one of the first directions of a lamella plate with the generation point, the intensity is reduced by outer border regions of the form filter.

8. The method of claim 7, wherein the intensity over an entire region of the form filter is reduced by a rotation of the form filter without maintaining the alignment of a first direction of one of the plurality of lamella plates with the generation point.

9. A device for setting a spatial intensity distribution of an X-ray beam, comprising:
   a form filter including a plurality of lamella plates which taper to a focal point such that, for each of the plurality of lamella plates, at least one straight line running through a respective one of the plurality of lamella plates, and forming a first direction of the respective one of the plurality of lamella plates, is aligned with the focal point; and a control unit configured to set, via an alignment of the first directions of the plurality of lamella plates of the form filter relative to a path of the X-ray beam to absorb parts of the X-ray beam by the plurality of lamella plates, the spatial intensity distribution of the X-ray beam.

10. The device of claim 9, wherein the plurality of lamella plates are designed and aligned such that a second direction is definable in each of the plurality of lamella plates, perpendicular to the first direction, using a straight line running through a respective one of each of the plurality of lamella plates, and wherein for each pair of lamella plates, of the plurality of lamella plates, the respective second directions are parallel to each other.

11. The device of claim 10, wherein the plurality of lamella plates describe circumferential surfaces of a set of concentric truncated cones.

12. The device of claim 9, further comprising:

a second plurality of lamella plates which taper to the focal point such that, for each of the second plurality of lamella plates, at least one straight line, running through a respective one of the plurality of second lamella plates and forming a first direction of the respective one of the plurality of second lamella plates, is aligned with the focal point, and wherein the plurality of lamella plates intersect the second plurality of lamella plates.

13. The device of claim 12, wherein the plurality of lamella plates describe circumferential surfaces of a set of concentric truncated cones.

14. The device of claim 9, wherein the plurality of lamella plates describe circumferential surfaces of a set of concentric truncated cones.

15. A method for setting a spatial absorption profile of an X-ray beam, comprising:

generating an X-ray beam via an X-ray tube;

guiding a beam path of the X-ray beam in a direction of propagation by a form filter including a plurality of lamella plates which taper to a focal point such that, for each respective lamella plate of the plurality of lamella plates, at least one straight line running through each respective lamella plate and forming a first direction of the lamella plate is aligned with the focal point;

aligning the first directions of the plurality of lamella plates of the form filter relative to the beam path, parts of the X-ray beam being absorbed as a result of the aligning of the first directions by the lamella plates; and setting the spatial absorption profile of the X-ray beam in a direction of propagation established by absorption of the parts of the X-ray beam due to the aligning of the first directions by the plurality of lamella plates.

16. A device for setting a spatial absorption profile of an X-ray beam, comprising:

a form filter including a plurality of lamella plates which taper to a focal point such that, for each of the plurality of lamella plates, at least one straight line running through a respective one of the plurality of lamella plates, and forming a first direction of the respective one of the plurality of lamella plates, is aligned with the focal point; and a control unit configured to set, via an alignment of the first directions of the plurality of lamella plates of the form filter relative to a path of the X-ray beam to absorb parts of the X-ray beam by the plurality of lamella plates, the spatial absorption profile of the X-ray beam.

17. The device of claim 16, wherein the plurality of lamella plates are designed and aligned such that a second direction is definable in each of the plurality of lamella plates, perpendicular to the first direction, using a straight line running through a respective one of each of the plurality of lamella plates, and wherein for each pair of lamella plates, of the plurality of lamella plates, the respective second directions are parallel to each other.

18. The device of claim 16, further comprising:

a second plurality of lamella plates which taper to the focal point such that, for each of the second plurality of lamella plates, at least one straight line, running through a respective one of the plurality of second lamella plates and forming a first direction of the respective one of the plurality of second lamella plates, is aligned with the focal point, and wherein the plurality of lamella plates intersect the second plurality of lamella plates.

19. The device of claim 16, wherein the plurality of lamella plates describe circumferential surfaces of a set of concentric truncated cones.

* * * * *